(12) United States Patent
Mark

(10) Patent No.: US 8,111,391 B2
(45) Date of Patent: Feb. 7, 2012

(54) OPTICAL CELL

(76) Inventor: Howard L. Mark, Suffern, NY (US)

( * ) Notice: Subject to any disclaimer, the term of this patent is extended or adjusted under 35 U.S.C. 154(b) by 523 days.

(21) Appl. No.: 11/745,926

(22) Filed: May 8, 2007

(65) Prior Publication Data

US 2007/0285656 A1    Dec. 13, 2007

Related U.S. Application Data

(60) Provisional application No. 60/808,882, filed on May 26, 2006.

(51) Int. Cl.
*G01J 3/00* (2006.01)
(52) U.S. Cl. ........ 356/300; 257/678; 257/680; 356/246; 356/436
(58) Field of Classification Search .......... 257/678, 257/680; 356/300, 246, 244, 436
See application file for complete search history.

(56) References Cited

U.S. PATENT DOCUMENTS

| 5,371,585 A * | 12/1994 | Morgan et al. | 356/246 |
| 5,815,258 A * | 9/1998 | Nakanishi | 356/246 |
| 5,949,536 A * | 9/1999 | Mark | 356/246 |

* cited by examiner

*Primary Examiner* — Junghwa M Im
(74) *Attorney, Agent, or Firm* — St. Onge Steward Johnston & Reens LLC

(57) ABSTRACT

An optical cell for spectral analysis is disclosed generally comprising a monolithic cell body that transmits light, the cell body having an outer surface and a fluid channel for receiving a sample that defines an inner surface. The inner surface of said cell body includes a planar section, and the outer surface of said cell body likewise includes a planar section, which is adjacent and substantially parallel to the planar section of the inner surface. In certain embodiments, the ends of the channel are frustoconical, and ferrules are employed to secure sample inlet/outlet tubes to the cell.

23 Claims, 4 Drawing Sheets

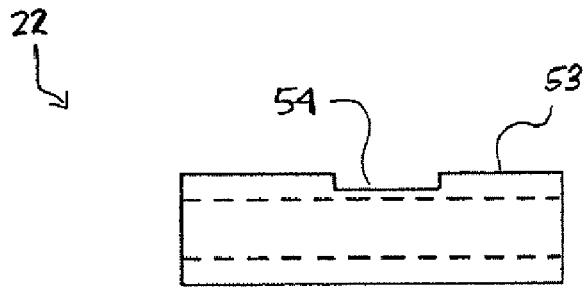 
FIG. 3A  FIG. 3B
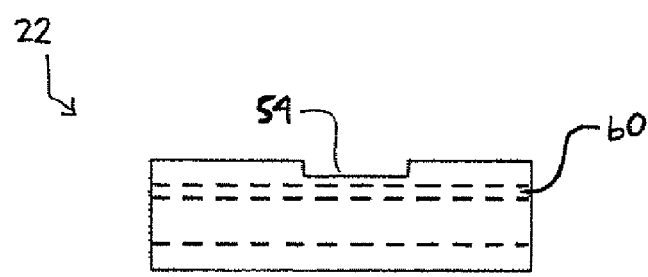 
FIG. 4A  FIG. 4B
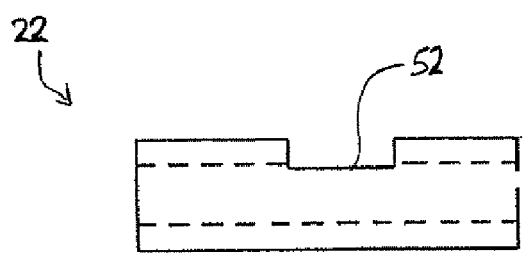 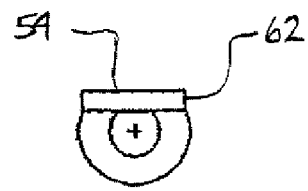
FIG. 5A  FIG. 5B

OPTICAL CELL

CROSS-REFERENCE TO RELATED APPLICATIONS

This patent application claims the benefit of, under Title 35, United States Code, Section 119(e), U.S. Provisional Patent Application No. 60/808,882, filed May 26, 2006.

FIELD OF THE INVENTION

The present invention relates to an optical cell for housing a sample. More specifically, the invention relates to a high-pressure optical cell for spectroscopic analyzers.

BACKGROUND OF THE INVENTION

Optical cells for housing samples during spectroscopic analyses are generally well known in the art. These devices facilitate in-line spectroscopic analysis of chemical samples, which is an important function in the chemical processing industry. In-line spectroscopic analysis enables the real-time determination of chemical content and concentration of chemical samples, both qualitatively and quantitatively, as the chemical is being generated and used in a chemical process.

Typically, a spectroscopic analyzer will employ an optical cell, an apparatus for introducing a chemical sample into the cell, a light source shining on the cell, and data collection and analysis instrumentation. Optical cells are available for use with various light sources, sample types, sample introduction methods, and collection and analysis modules, and may be used for either gaseous or liquid sample analysis. These cells are often used for off-line batch sample analysis, but in-line optical analysis cells with limited performance characteristics also exist. The optical cell itself is used to hold the sample adjacent to the light source during the analysis of the chemical sample. Known prior art optical cells typically use windows comprising a light transmitting material sealed to a pressure resistant housing.

These types of optical cells result in a number of disadvantages. Most significantly, sample fluids will often leak from the cells, especially at high-pressures, thereby soiling and/or damaging instruments, skewing test results, and/or necessitating time consuming cleanup procedures. This occurs because it is difficult to achieve a leak-free seal between metal cell-housings and the light-transmitting material. While in some cases, fused seals are used to provide leak-free operation, these applications are limited to batch measurement, result in undesirable dead volume, and/or are not readily reusable due to the time and expense required for cleaning. More generally, such cells comprise numerous parts and are unnecessarily complex. Such arrangements generally include at least two crystalline windows, two-piece adjustable housings, and two-piece fused cells. This abundance of parts increases the possibility of leaking, especially at high pressures.

Accordingly, it has been suggested to use an optical cell formed from a monolithic crystal, to which the sample inlet and outlet tubes are sealed, such as that disclosed in U.S. Pat. No. 5,949,536 to Mark, the specification of which is hereby incorporated by reference. This optical cell solves many of the disadvantages inherent in previous optical cell designs, including the assembly of separate parts and the undesirable leakage that often results.

The use of these optical cells, however, can be limited in terms of the applications in which they can be employed. An improved optical cell, which allows one to look into the cell, rather than being limited to spectra transmitted through the cell, would allow one to measure the spectra of samples within the cell using reflection methods, or Raman spectroscopy, while being able to see a clear image of the sample housed in the cell.

What is desired, therefore, is an optical cell for spectroscopic analyzers that performs well at high pressures. What is further desired is an optical cell that is not limited to spectroscopic applications that collect spectra through the cell. What is also desired is an optical cell that is inexpensive, is easy to assemble and clean, and minimizes undesirable dead zone.

SUMMARY OF THE INVENTION

Accordingly, it is an object of the present invention to provide an optical cell for a spectroscopic analyzer with a window that facilitates additional ways of measuring spectra.

It is a further object of the present invention to provide an optical cell for a spectroscopic analyzer that does not leak.

It is yet another object of the present invention to provide an optical cell for a spectroscopic analyzer that minimizes the number of parts employed.

It is still another object of the present invention to an optical cell for a spectroscopic analyzer that is easy to assemble, use, and clean, and that minimizes dead volume.

In order to overcome the deficiencies of the prior art and to achieve at least some of the objects and advantages listed, the invention comprises a method of housing a spectroscopic sample, including providing a monolithic cell body that transmits light, wherein the cell body has an outer surface, forming a fluid channel in the cell body that defines an inner surface of the cell body, wherein a portion of the inner surface has a planar section, and forming a planar section on the outer surface of the cell body that is adjacent and substantially parallel to the planar section of the inner surface of the cell body.

In another embodiment, the invention comprises an optical cell for a spectroscopic analyzer, including a monolithic cell body that transmits light, the cell body having an outer surface, wherein the cell body has a fluid channel for receiving a sample, the channel defining an inner surface of the cell body, wherein the inner surface of the cell body includes a planar section, and wherein the outer surface of the cell body has a planar section adjacent and substantially parallel to the planar section of the inner surface of the cell body.

In yet another embodiment, the invention comprises a spectroscopic analyzer, including a light-transmitting cell body having first and second ends, wherein the cell body has a fluid channel extending therethrough from the first end to the second end, wherein the fluid channel has a planar wall portion, and wherein the outer surface of the crystal includes a recess, the recess having a planar surface adjacent and substantially parallel to the planar wall portion of the fluid channel.

In certain embodiments, the step of forming the planar section of the outer surface of the cell body comprises forming a recess in the outer surface of the cell body. In some of these embodiments, the step of forming the fluid channel comprises forming a bore with an arcuate wall and a planar wall through the cell body, such that the planar wall comprises the planar section of the inner surface of the cell body, while in others of these embodiments, the step of forming the fluid channel comprises forming a bore in the cell body, disposing an insert that transmits light in the bore, wherein the insert has an arcuate surface corresponding to bore and a planar surface that comprises the planar section of the inner surface of the cell body, and fusing the insert to the cell body. In yet other embodiments, the step of forming the fluid channel comprises forming a bore in the cell body, removing a portion of the cell body to expose the bore, positioning a substantially rectangular block that transmits light over the exposed portion of the bore, wherein the block has first and second planar faces that comprise the planar sections of the inner and outer surfaces, respectively, of the cell body, and fusing the block to the cell body.

In certain embodiments, the invention further includes the step of polishing at least one of the planar sections of the inner and outer surfaces. In some embodiments the cell body comprises sapphire, while in other embodiments, it comprises quartz, glass, or plastic.

In certain embodiments, the fluid channel has first and second frustoconical ends. In some of these embodiments, the invention further includes disposing the end of a sample inlet tube into the first end of the fluid channel, disposing the end of a sample outlet tube into the second end of the fluid channel, and positioning first and second ferrules over the inlet and outlet tubes and pushing the first and second ferrules into the first and second frustoconical ends, respectively, to seal the inlet and outlet tubes to the cell body. In other embodiments, the invention includes providing sample inlet and outlet tubes each having a channel therethough with a frustoconical end, disposing the first end of the cell body in the frustoconical end of the channel of the sample inlet tube, disposing the second end of the cell body in the frustoconical end of the channel of the sample outlet tube, and positioning first and second ferrules over the cell body and pushing the first and second ferrules into the frustoconical ends of the inlet and outlet tubes, respectively, to seal the cell body to the inlet and outlet sample tubes.

In some embodiments, the invention further includes disposing the cell body in a housing having a wall, thereby forming a chamber between the housing wall and the cell body, and flushing the chamber with a fluid.

BRIEF DESCRIPTION OF THE DRAWINGS

FIGS. 3A-B are schematic views showing further details of the optical cell of FIGS. 2A-C.

FIGS. 4A-B are schematic views showing further details of the optical cell of FIGS. 2A-C.

FIGS. 5A-B are schematic views showing further details of the optical cell of FIGS. 2A-C.

DETAILED DESCRIPTION OF THE INVENTION

Figure 1:
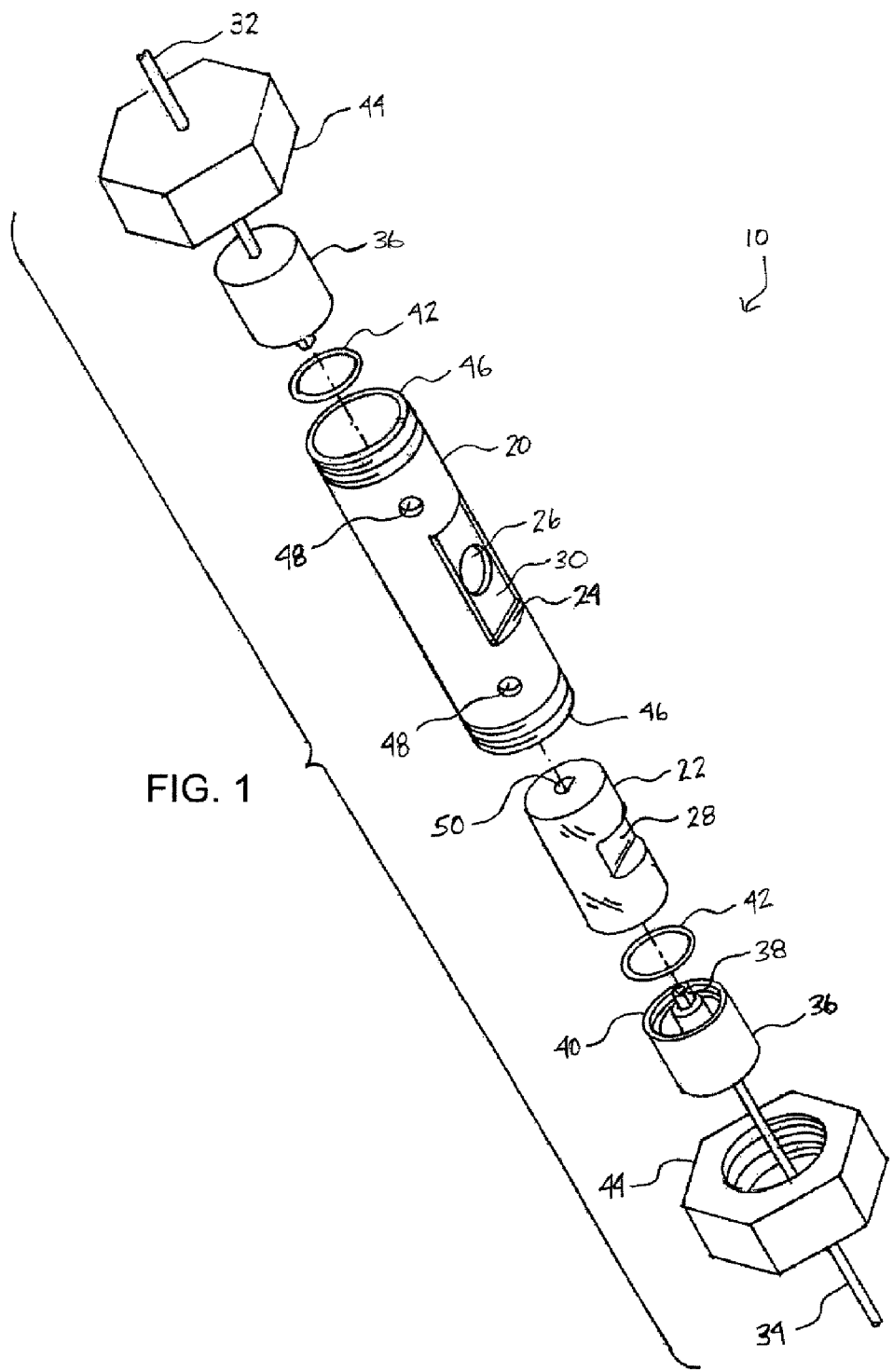
FIG. 1 is an exploded, isometric view of optical cell assembly in accordance with the invention.

The basic components of one embodiment of an optical cell assembly for a spectral analyzer in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

In the embodiment depicted in FIG. 1, the assembly 10 includes a substantially cylindrical housing 20 fashioned from a suitable material, such as stainless steel, and a substantially cylindrical optical cell 22 disposed in the housing 20. The housing 20 includes recessed portion 24, which includes an aperture 26, such that, when the cell 22 is disposed in the housing 20, the aperture 26 aligns with a window portion 28 of the cell, which is further described in more detail below. In some embodiments, a thin cover 30, such a microscope cover slip, is placed in the recessed portion 24 of the housing 20. The cover may comprise sapphire, quartz, or other suitable transparent material.

First and second inlet/outlet tubes 32, 34 are coupled to the optical cell 22 for supplying and removing a sample fluid. It should be noted that the use of the terms "inlet" and "outlet" for these tubes is not intended to imply that either tube necessarily serves only as an inlet or as an outlet, and the use of term "inlet/outlet" is likewise not intended to imply that either tube must be both an inlet and an outlet. In other words, these terms are used in an inclusive sense, and an inlet tube may also serve as an outlet tube, while an outlet tube may also serve as an inlet tube. Thus, for example, in the case of an in-line analysis, tube 32 may serve to introduce the sample into the cell 22, and the sample may exit through the tube 34. However, in other embodiments, the sample may be introduced into the sample cell by one or both of the tubes 32 and 34, and may then leave the cell 22 via one or both of the tubes 32, 34.

In certain embodiments, the tubes 32, 34 are coupled to the optical cell 22 via inserts 36, each of which has a tip 38 that corresponds to the shape of a channel 50 in the optical cell 22. In some of these embodiments, the insert 36 has an outer rim 40 that fits over the end of the cell 22, and O-rings 42 are employed to provide a seal between the insert 36 and the cell 22. Caps 44 are screwed onto the threaded ends 46 of the housing 20 to secure the rest of the assembly together.

When certain materials from which the cell body 22 may be formed, such as fused quartz, are heated to a high temperature, they can react with atmospheric moisture, which can damage the cell. To prevent this, in certain embodiments, the cell is surrounded with a shroud that can be flushed with dry air, nitrogen, or other gas, in order to keep moisture away from the cell body 22. This shroud may, for example, comprise the housing 20, which can be achieved by leaving some clearance between the housing 20 and cell body 22, and providing gas inlet/outlets 48 in the housing for providing the flushing gas.

Figure 2A:
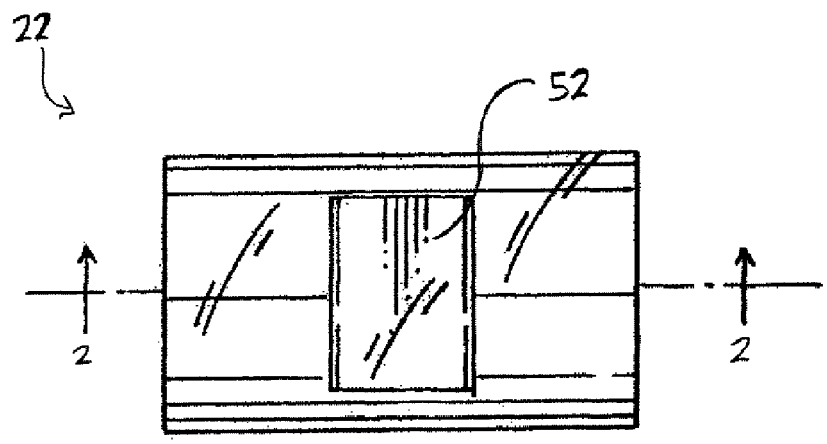
FIG. 2A is a top view of the optical cell of the assembly of FIG. 1.
Figure 2B:
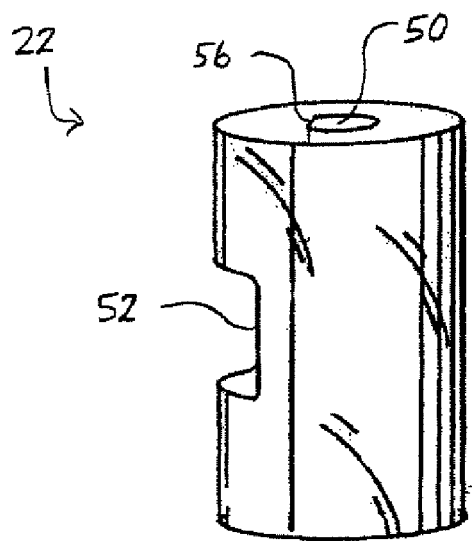
FIG. 2B is an isometric view of the optical cell of FIG. 2A.
Figure 2C:
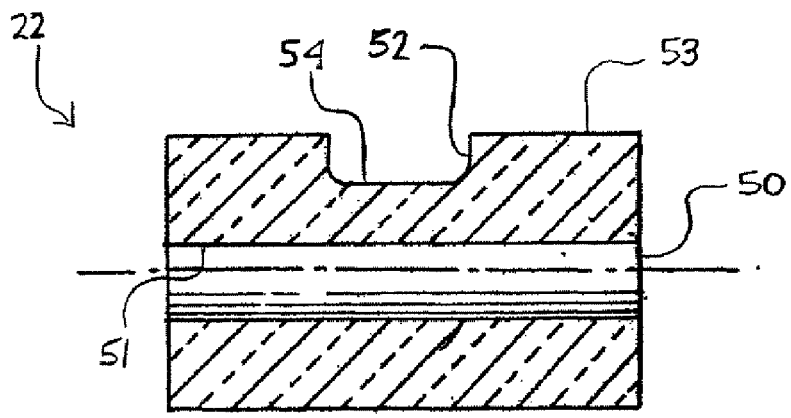
FIG. 2C is a side, cross-sectional view of the optical cell of FIG. 2A along the plane 2-2.

Referring now to FIGS. 2A-C, the optical cell 22 comprises a monolithic piece of light transmitting material, which may, for example, comprise a crystal, such as sapphire. In other embodiments, however, the monolithic cell body 22 may comprise any material suitable for transmitting light, such as fused quartz, glass, or even plastic. In some cases, transparency in spectral regions other than visible light, such as infrared, may be desired, which would require the use of a material that is transparent in the appropriate spectral region.

The cell body 22 has a channel 50 therein, which forms an inner surface 51 of the cell body. Likewise, the cell has an outer surface 53, which has a planar section 54. As noted above, in certain embodiments, the cell body 22 is substantially cylindrical, and the planar section 54 is the result of a recess or notch 52 formed in the outer surface 53 of the cell body 22. The inner surface 51 of the cell body likewise has a planar section 56, which is adjacent and substantially parallel to the planar section 54 of the outer surface 53.

Methods for forming the planar section 56 are illustrated in more detail in FIGS. 3-5. Referring first to FIGS. 3A-B, in certain embodiments, the planar surface 56 results from forming a bore within the cell body that has a flat portion 56. As shown in FIGS. 4A-B, in other embodiments, the inner surface 56 is created by forming a cylindrical bore in or otherwise providing a tubular cell body 22, and then disposing an insert 60 in the bore, where the insert 60 has a flat surface (which may be polished) and an arcuate surface corresponding to the wall of the bore. The insert 60 is then fused to the cell body 22 to create a monolithic piece. Though the insert 60 may be as long as the cell body 22, a length sufficient to cover the window area will suffice.

As illustrated in FIGS. 5A-B, in still other embodiments, the inner surface 56 of the channel 50 is created by providing a tubular cell body 22, and then, creating a deeper recess 52. Specifically, instead of creating a recess 54 in the outer surface 53 of the cell body 22 that stops before reaching inner bore wall or insert 60, as shown in FIGS. 3-4, a recess 52 is formed that extends down completely through the tube wall and exposes the inner bore, as illustrated in FIG. 5A. As shown in FIG. 5B, a flat, rectangular block 62 (which may be polished on both sides), which has a length corresponding to the length of the recess 52, is then disposed in the recess 52, the first and second flat planar faces of the block 62 forming the outer and inner planar surfaces 54, 56. The block 60 is fused to the cell body 22, and the squared pieces sticking out from the tube can then be ground away so that they match the radius of the cell body, if desired.

As a result of the aforementioned planar surfaces created on the inner and outer surfaces 51, 53 of the cell body 22, the cell body 22 ends up with a window area that is flat on both the inside and outside, which in certain advantageous embodiments, is polished on both sides. As a result, a window area for looking into the cell that is integrally formed with the monolithic cell body is thereby provided. Additionally, it should be noted that more than one window can be provided on the optical cell in this manner, arranged either longitudinally along the length of the cell body 22 or around its circumference.

In some embodiments, the cell body 22 is made sufficiently long so that the viewing region can be heated, while the ends of the cell body 22 can remain cool enough that the seals will not be damaged by the heat. Additionally, in certain advantageous embodiments, other methods of coupling the cell body to the sample inlet/outlet tubes are employed such that no housing and concomitant connecting/sealing parts are required. Specifically, several implementations of the use of ferrules may be employed for this purpose.

Figure 6:
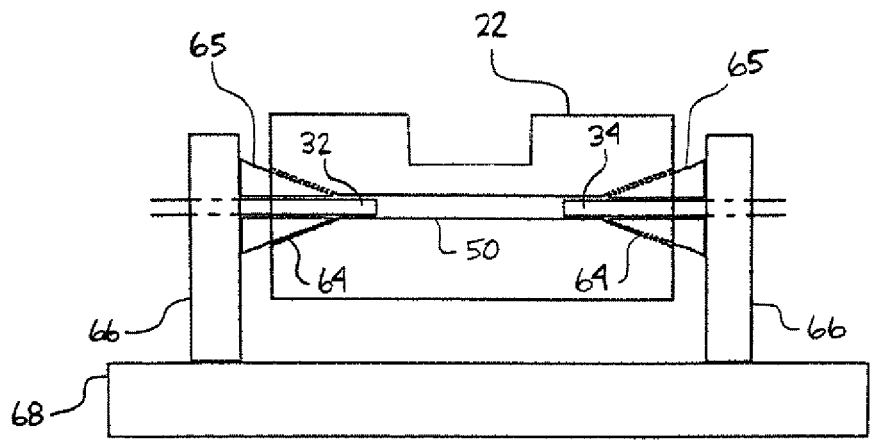
FIG. 6 is a schematic view of the optical cell of FIGS. 2A-C secured to sample inlet/outlet tubes using ferrules.

Referring to FIG. 6, in certain advantageous embodiments, the channel 50 of the cell body has first and second frustoconical ends 64. The ends of the sample inlet/outlet tubes 32, 34 are disposed in the ends of the cell body 22, and ferrules 65 are then positioned over the tubes 32, 34. Axially forces are applied to the ferrules, forcing them into the frustoconical ends of the channel 50 and compressing them around the tubing.

Figure 7:
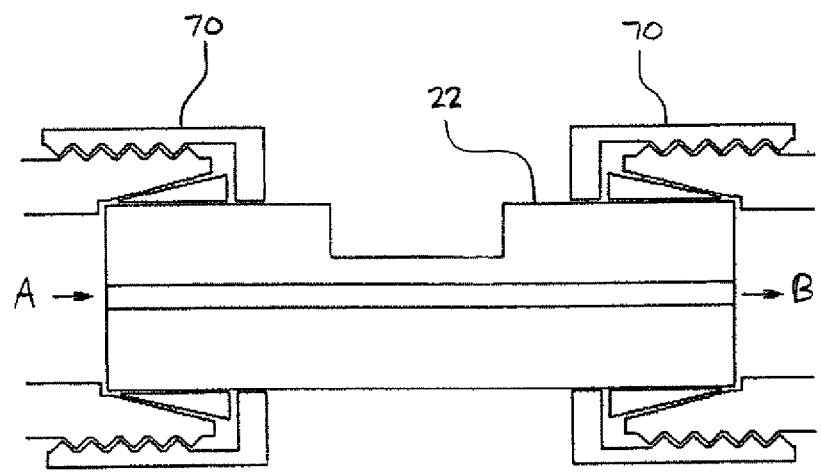
FIG. 7 is a schematic view of the optical cell of FIGS. 2A-C secured to sample inlet/outlet tubes using ferrules.

Any external framework can employed for applying the necessary forces on the ferrules. For example, as shown in FIG. 6, the forces needed to press the ferrules into the crystal are applied by two external arms 66, which are, in turn, connected to a base plate 68, comprising a vise-like device. Alternatively, as shown in FIG. 7, the ferrules are used to seal the crystal to external tubing by positioning the ferrule over the outside of the crystal. In the embodiment illustrated in FIG. 7, caps 70 are screwed onto threaded ends of the inlet/outlet tubes to apply the necessary forces to the ferrules to secure the tubes to the cell body 22.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of housing a spectroscopic sample, the method comprising:
   providing a monolithic tubular cell body that transmits light, wherein the tubular cell body has an outer surface;
   forming a fluid channel in the cell body that defines an inner surface of the cell body, wherein a portion of the inner surface has a planar section, and wherein a portion of the inner surface has an arcuate wall, such that the planar wall is flat and comprises the planar section of the inner surface of the cell body; and
   forming a single planar section on the outer surface of the cell body that is adjacent and substantially parallel to the planar section of the inner surface of the cell body,
   forming a recess in the outer surface of the cell body that stops before reaching the inner surface of the cell body, and
   viewing the spectroscopic sample.

2. The method of claim 1, wherein the step of forming a fluid channel comprises:
   forming a bore in the cell body;
   disposing an insert that transmits light in the bore, wherein the insert has an arcuate surface corresponding to the bore and a planar surface that comprises the planar section of the inner surface of the cell body; and
   fusing the insert to the cell body.

3. The method of claim 1, wherein the step of forming a fluid channel comprises:
   forming a bore in the cell body;
   removing a portion of the cell body to expose the bore;
   positioning a substantially rectangular block that transmits light over the exposed portion of the bore, wherein the block has first and second planar faces that comprise the planar sections of the inner and outer surfaces, respectively, of the cell body; and
   fusing the block to the cell body.

4. The method of claim 1, further comprising the step of polishing at least one of the planar sections of the inner and outer surfaces.

5. The method of claim 1, wherein the fluid channel has first and second frustoconical ends, further comprising the steps of:
   disposing the end of a sample inlet tube into the first end of the fluid channel;
   disposing the end of a sample outlet tube into the second end of the fluid channel; and
   positioning first and second ferrules over the inlet and outlet tubes and pushing the first and second ferrules into the first and second frustoconical ends, respectively, to seal the inlet and outlet tubes to the cell body.

6. The method of claim 1, wherein the cell body has first and second ends, further comprising the steps of:
   providing sample inlet and outlet tubes each having a channel therethough with a frustoconical end;
   disposing the first end of the cell body in the frustoconical end of the channel of the sample inlet tube;
   disposing the second end of the cell body in the frustoconical end of the channel of the sample outlet tube; and positioning first and second ferrules over the cell body and pushing the first and second ferrules into the frustoconical ends of the inlet and outlet tubes, respectively, to seal the cell body to the inlet and outlet sample tubes.

7. The method of claim 1, further comprising the steps of:
disposing the cell body in a housing having a wall, thereby forming a chamber between the housing wall and the cell body; and
flushing the chamber with a fluid.

8. An optical cell for a spectroscopic analyzer, comprising:
a monolithic tubular cell body that transmits light, said tubular cell body having an outer surface;
wherein said cell body has a fluid channel for receiving a sample, said channel defining an inner surface of said cell body;
wherein the inner surface of said cell body includes a planar section, and wherein a portion of the inner surface has an arcuate wall and a planar wall, such that the planar wall is flat and comprises the planar section of the inner surface of the cell body; and
wherein the outer surface of said cell body has a single planar section adjacent and substantially parallel to the planar section of the inner surface of said cell body, and
wherein a recess is formed in the outer surface of the cell body that stops before reaching an inner surface of the cell body.

9. The optical cell of claim 8, wherein said cell body comprises sapphire.

10. The optical cell of claim 8, wherein said cell body comprises quartz, glass, or plastic.

11. The optical cell of claim 8, wherein the outer surface of said crystal includes a recess having a planar surface, said planar surface comprising the planar section of the outer surface of said cell body.

12. The optical cell of claim 11, wherein said fluid channel comprises a bore extending through said cell body, said bore defining the planar section of the inner surface of said cell body.

13. The optical cell of claim 11, wherein said fluid channel comprises a bore defined by an inner wall of said cell body and an insert disposed in said bore and fused to said cell body, the planar section of the inner surface of said cell body comprising the planar surface of said insert.

14. The optical cell of claim 8, wherein:
said fluid channel comprises a bore defined by an inner wall of said cell body and a first planar face of a substantially rectangular block fused to said cell body; and
the planar section of the outer surface of said cell body comprises a second planar face of said substantially rectangular block fused to said cell body.

15. The optical cell of claim 8, wherein said fluid channel has first and second frustoconical ends.

16. A spectroscopic analyzer, comprising:
a light-transmitting tubular monolithic cell body having first and second ends;
wherein said tubular cell body has a fluid channel extending therethrough from said first end to said second end;
wherein said fluid channel has a planar wall portion, and wherein a portion of an inner surface of the cell body has an arcuate wall and a planar wall, such that the planar wall is flat and comprises the planar section of the inner surface of the cell body; and
wherein the outer surface of said tubular monolithic cell body includes a recess, said recess having a planar surface adjacent and substantially parallel to the planar wall portion of said fluid channel, said recess stopping before reaching an inner surface of the cell body.

17. The spectral analyzer of claim 16, wherein said fluid channel has first and second frustoconical ends, further comprising:
a sample inlet tube having an end disposed in the first end of said fluid channel;
a sample outlet tube having an end disposed in the second end of said fluid channel; and
first and second ferrules positioned over said inlet and outlet tubes and disposed in the first and second frustoconical ends, respectively, of said fluid channel for sealing said inlet and outlet tubes to said cell body.

18. The spectral analyzer of claim 16, further comprising:
sample inlet and outlet tubes each having a channel therethrough with a frustoconical end;
wherein the first end of said cell body is disposed in the frustoconical end of the channel of said sample inlet tube;
wherein the second end of said cell body is disposed in the frustoconical end of the channel of said sample outlet tube; and
first and second ferrules positioned over the cell body and disposed in the frustoconical ends of the inlet and outlet samples tubes, respectively, for sealing the cell body to said inlet and outlet tubes.

19. The spectral analyzer of claim 16, wherein said cell body comprises sapphire.

20. The spectral analyzer of claim 16, wherein said cell body comprises quartz, glass, or plastic.

21. The method of claim 1, wherein the fluid channel has the shape of a flat half oval.

22. An optical cell of claim 8, wherein the fluid channel has the shape of a flat half oval.

23. The optical cell of claim 8, the optical cell being adapted to work at high pressures.

* * * * *